US008797350B2

(12) United States Patent
Fram

(10) Patent No.: US 8,797,350 B2
(45) Date of Patent: Aug. 5, 2014

(54) DYNAMIC CUSTOMIZABLE HUMAN-COMPUTER INTERACTION BEHAVIOR

(75) Inventor: Evan K. Fram, Paradise Valley, AZ (US)

(73) Assignee: Dr Systems, Inc., San Diego, CA (US)

( * ) Notice: Subject to any disclaimer, the term of this patent is extended or adjusted under 35 U.S.C. 154(b) by 210 days.

(21) Appl. No.: 13/331,651

(22) Filed: Dec. 20, 2011

(65) Prior Publication Data
US 2012/0154431 A1 Jun. 21, 2012

Related U.S. Application Data

(60) Provisional application No. 61/425,156, filed on Dec. 20, 2010.

(51) Int. Cl.
*G09G 5/00* (2006.01)
*G06F 3/00* (2006.01)

(52) U.S. Cl.
USPC .......................... 345/619; 715/707; 715/745

(58) Field of Classification Search
None
See application file for complete search history.

(56) References Cited

U.S. PATENT DOCUMENTS

| 5,374,942 A * | 12/1994 | Gilligan et al. ............... 345/157 |
| 7,327,348 B2 * | 2/2008 | Goldenberg et al. ......... 345/156 |
| 2003/0217892 A1 * | 11/2003 | Persky ............................. 186/68 |
| 2008/0235583 A1 * | 9/2008 | Ostergaard et al. ........... 715/716 |
| 2010/0235794 A1 * | 9/2010 | Ording ........................... 715/863 |
| 2011/0041077 A1 * | 2/2011 | Reiner ........................... 715/745 |

* cited by examiner

*Primary Examiner* — Joni Richer
*Assistant Examiner* — Yi Wang
(74) *Attorney, Agent, or Firm* — Knobbe, Martens, Olson & Bear, LLP

(57) ABSTRACT

Systems and methods for customizing behavior of a computing system based on details of interactions with the computing system by a user, such as a direction, intensity, or magnitude of a particular input from a user input device.

21 Claims, 16 Drawing Sheets

390 →

Behavior B1

| Tilt range (degrees) | Display rate (images/sec) |
|---|---|
| 0    4 | 0 |
| 5    9 | 5 |
| 10   24 | 10 |
| 25   39 | 15 |
| 40   90 | 20 |

Behavior B2

| Tilt range (degrees) | Display rate (images/sec) |
|---|---|
| 0    4 | 0 |
| 5    9 | 8 |
| 10   24 | 12 |
| 25   39 | 18 |
| 40   90 | 22 |

392 →

Modifier M1
Decrease display rate by 20%

Modifier M2
Decrease display rate by 50%

Modifier M3
Cap display rate at 8 images/second

Modifier M4
Cap display rate at 20 images/second

394 →

Condition C1
Use Behavior B1 as default

Condition C2
If Exam is a CTA then use Behavior B2

Condition C3
If displayed image is > 1 megapixel then apply Modifier M1

Condition C4
If within 2 images of an image marked positive by CAD then apply Modifier M2

Condition C5
If modality is CT and displayed as Soft Tissue Window/Level then use Behavior B2

Condition C6
If the clinical history is known or suspected cancer then apply Modifier M2

Fig. 5a

DYNAMIC CUSTOMIZABLE HUMAN-COMPUTER INTERACTION BEHAVIOR

CROSS-REFERENCE TO RELATED APPLICATIONS

This application claims the benefit of priority under 35 U.S.C. §119(e) of U.S. Provisional Application No. 61/425,156, filed Dec. 20, 2010, the disclosure of which is hereby incorporated by reference in its entirety.

BACKGROUND

There are many situations in which users employ computing systems to view information where it is important that the users accurately and efficiently interpret that information. Current computing systems are capable of presenting information at rates that exceed a user's perceptual ability to accurately interpret the information presented, resulting in errors. This problem will increase in severity as computer processing power and bandwidth continue to increase.

SUMMARY

For purposes of this summary, certain aspects, advantages, and novel features are described herein. It is to be understood that not necessarily all such advantages may be achieved in accordance with any particular embodiment. Thus, for example, those skilled in the art will recognize that the invention may be embodied or carried out in a manner that achieves one advantage or group of advantages as taught herein without necessarily achieving other advantages as may be taught or suggested herein.

Disclosed herein are systems and methods for operating a computing device so that the speed of information presentation is matched to the user's preferences and/or to various factors that may impact the user's ability to accurately and efficiently interpret it, including properties of the visual information, properties of the display device, environmental factors, characteristics of the user, such as expertise and fatigue, and any other factors that may be relevant to the user's review of the information.

In one embodiment, a computing system comprises one or more hardware processors configured to execute software instructions stored in modules and a tangible computer readable medium storing modules configured for execution by the one or more hardware processors. In one embodiment, the modules include a display module configured to display medical images on a display device of the computing system and a control module configured to: access a data structure storing conditions associated with respective behavior models; identify one or more of the conditions that are matched by one or more characteristics associated with exam viewing, the computing system, an environment surrounding the computing system, the display device, bandwidth available to the computing system, the medical images, a patient, a medical history of the patient, an input device, and/or a user of the computing system, wherein at least one of the identified conditions is associated with a display behavior including two or more rates of display of medical images associated with respective levels of interaction with an input device; receive data from an input devices indicating a level of interaction with the input device; determine a rate of display of medical images based on an association in the at least one of the identified conditions between the level of interaction and one of the two or more rates of display of medical images; and display the medical images at the determined rate.

BRIEF DESCRIPTION OF THE DRAWINGS

FIG. 5a illustrates information within an interaction behavior model.

Figure 1:
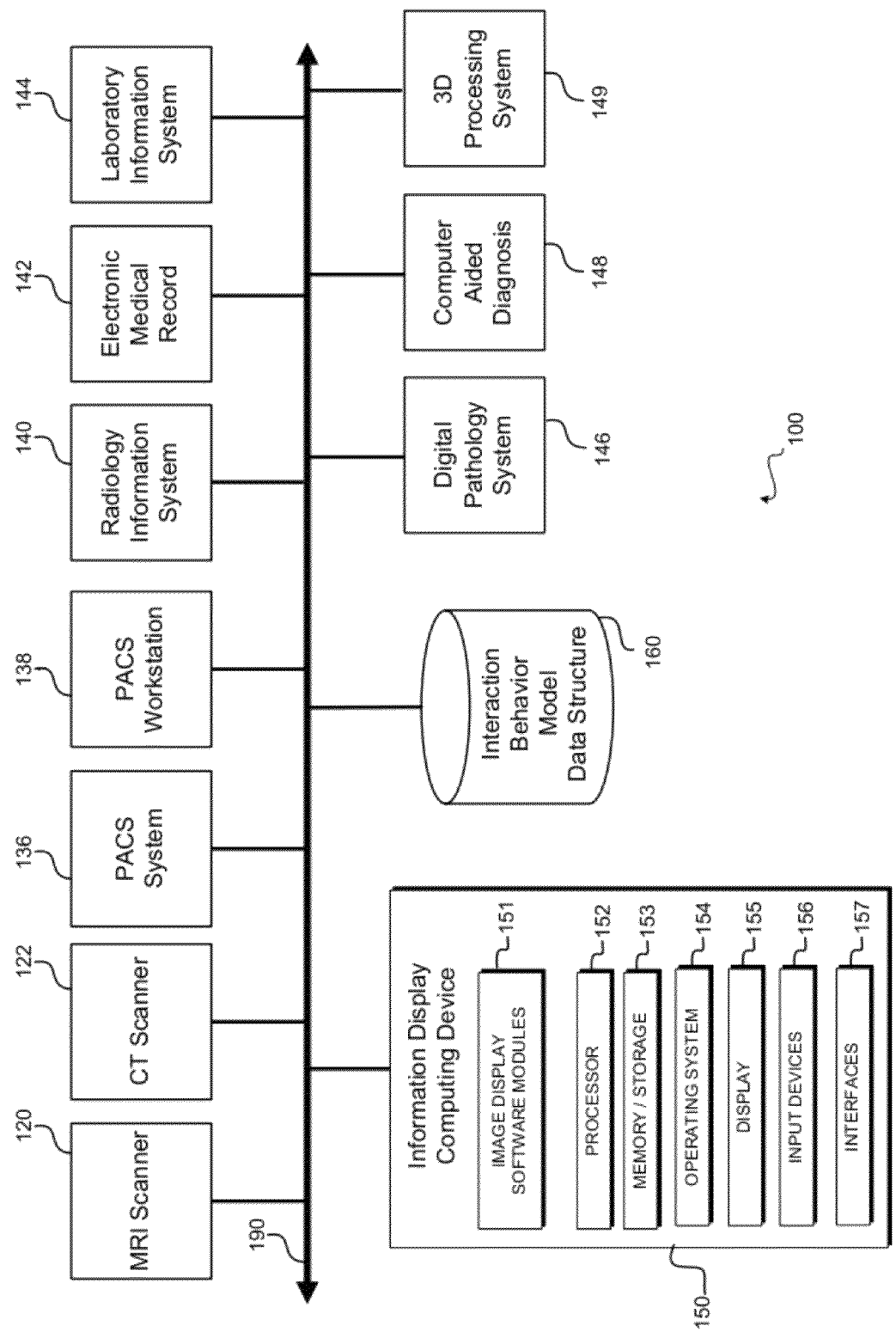
FIG. 1 is a block diagram illustrating one embodiment of a computing system that may be used to implement certain systems and methods described herein.

These and other features will now be described with reference to the drawings summarized above. The drawings and the associated descriptions are provided to illustrate certain embodiments of the invention and not to limit the scope of the

DETAILED DESCRIPTION

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Images

In the fields of radiology, cardiology, and pathology, for example, physicians often view a large amount of imaging information and it is critical that they accurately interpret the imaging information to make an accurate diagnosis. In addition, there are many other fields where accurate and efficient interpretation of imaging information is important, such as baggage screening, satellite imaging, seismic imaging used in oil and gas exploration, and surveillance video.

Medical imaging exams can be acquired by a number of different medical imaging techniques, including computed tomography (CT), magnetic resonance imaging (MRI), ultrasound, nuclear medicine, positron emission computed tomography (PET), digital angiography, mammography, computed radiography, digital radiography, fluoroscopy, and others such as images generated in medical pathology and endoscopy. A variety of computing systems are used to manage medical images, including storage, distribution, analysis, processing and display. These computing systems include Picture Archive and Communication Systems (PACS), Digital Pathology Systems, Cardiovascular Information Systems, Computer Aided Diagnosis Systems (CAD), 3D Processing systems, Electronic Medical Record (EMR) systems, standalone software for display of medical images, web based Personal Health Record (PHR) systems and other systems that manage medical imaging exams, such as online physician portals.

As described below, physicians and others utilize computing devices, herein referred to as information display computing devices, to view information. Information display computing devices can come in many forms and can be single computing devices or combinations of computing devices, including dedicated PACS workstations, Electronic Medical Record Systems, general purpose computing systems, computer tablets, and/or handheld devices such as smartphones.

Medical imaging exams often include a large number of images. For example, a computed tomography (CT) exam may include hundreds or thousands of images. Because it is usually impractical to view all of an exam's images simultaneously, the display of an information display computing device typically displays a fraction of the total number of images at once and allows the user to interact with the information display computing device to display other images or other portions of an image being displayed.

In addition, a medical image may include too many pixels to be displayed at the full or desired resolution on an information display computing device. For example, a single digital pathology image could include a trillion pixels, vastly exceeding the display resolution of a 1 megapixel monitor. The mismatch between the pixel size of the image and the pixel size of the display device requires the user to interact with the computing device to display various portions of the image.

Medical imaging exams are often divided into series, where a series comprises a group of one or more images acquired or displayed using a certain technique. Images within a series may differ in anatomic position or time of acquisition, for example. For example, in a computed tomography exam, one series might include 250 contiguous 0.6 mm thick images of the brain obtained without administration of intravenous contrast material. Another series might include 250 contiguous 0.6 mm thick images of the brain obtained during administration of intravenous contrast material. A brain MRI might include multiple series acquired with different technical parameters, possibly including images acquired before administration of intravenous contrast material and images acquired after administration of intravenous contrast material. For example a brain MRI might include the following series: Sagittal T1, axial T1, axial FLAIR, axial T2, axial diffusion, coronal gradient echo and post-contrast axial, sagittal and coronal T1 weighted images.

Figure 13:
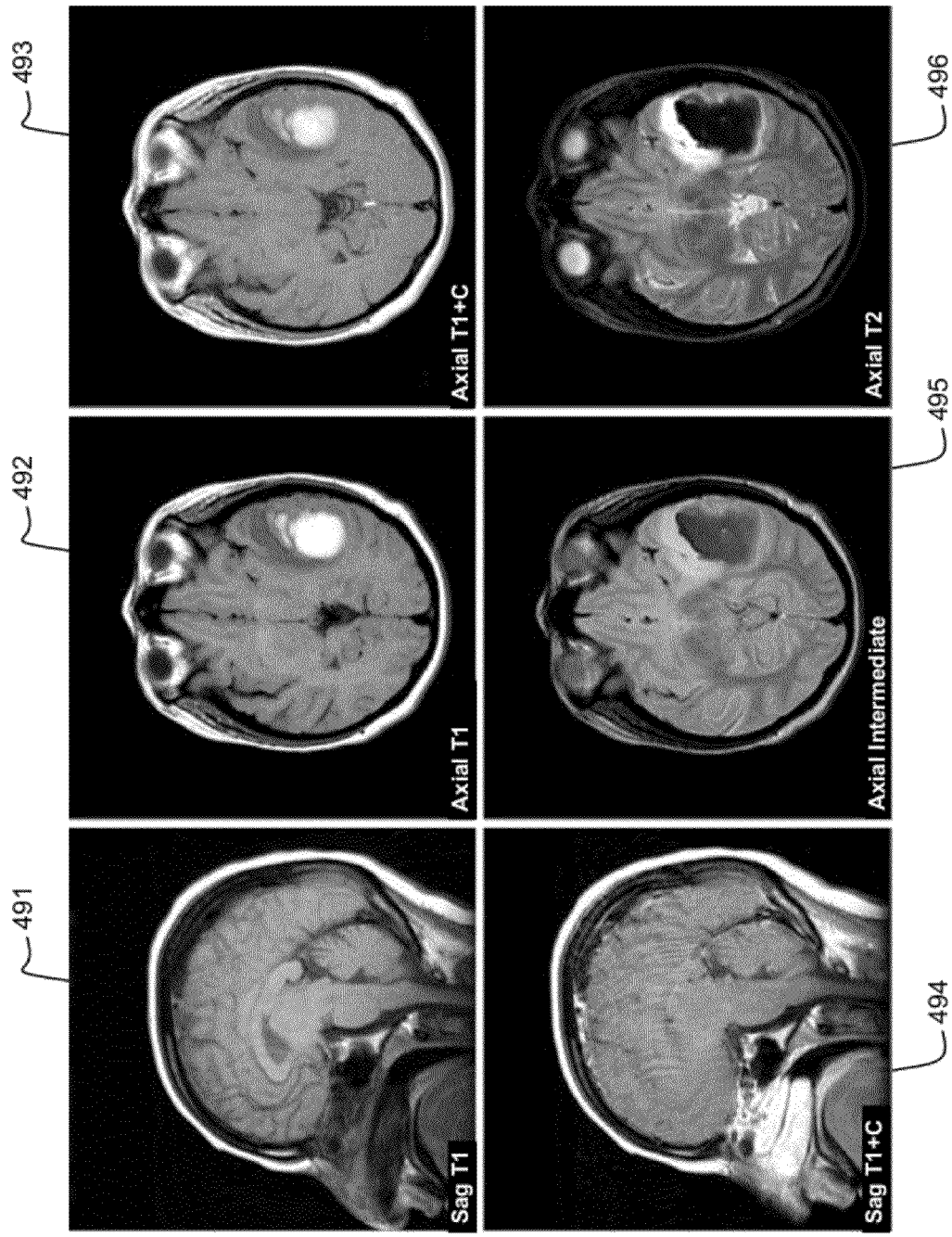
FIG. 13 displays six image frames as might be displayed on a display device, where each image frame displays an image from a different series from within one or more medical imaging exams.

Separate image series may be displayed in separate display frames on a display device, e.g., as illustrated in FIG. 13 where six series from a brain MRI are displayed as they might appear on an information display computing device. Depending on the input device and user preference, a number of methods can be used to allow the user to change the image within the series that is displayed in an image frame. The images within a series are typically numbered, for example 1 to 100 in a series with 100 images.

While much of the discussion herein refers to display of medical images, the systems and methods disclosed herein are not limited to such images. In fact, the systems and methods discussed herein may be applied to any type of information that is presented visually and controlled by any input device. For example, the systems and methods discussed herein may be used with images related to baggage screening, satellite imaging, seismic imaging used in oil and gas exploration, surveillance video, and/or any other type of images. Additionally, while visual information may be in the form of images, visual information may be in other forms. For example, visual information may be in graphical form, such as EKG and EEG information. Visual information may also be in the form of text, such as medical laboratory results, medical exam reports or documents utilized in legal proceedings. Visual information may also be presented in other forms or as a mixture of various forms, for example a multimedia web page comprising text, graphics, images, and/or animations. The systems and methods described here may be applied to any visual information presented on a computing device. Thus, any reference herein to medical images should be construed to cover other embodiments involving other image types.

Example Features of Certain Embodiments

In some embodiments, users may interact with computing systems via a wide range of input devices to control the presentation of information and/or to perform other functions. For any manipulation of a particular input device by a user, there are many potential actions that a computing device might take. For example, an input device might be utilized by a user to control the display of visual information on a computing device. In some embodiments, the systems and methods discussed herein modify the behavior of the computing device as a function of user input, accounting for factors such as properties of the visual information displayed, properties of the display device, environmental factors, user preference, and/or characteristics of the user such as expertise and fatigue.

In addition, users may interact with computing systems via a wide range of input devices to control the presentation of information or to perform other functions using computing devices. For any manipulation of a particular input device by a user, there are many potential actions that a computing device might take. For example, a user moving a joystick type device 5 degrees to the right center could result in many different actions. For example, it might result in serial presentation of images at a rate of 5 images/second, 10 images/second or 20 images/second.

There is a need for better methods for matching a user's manipulation of an input device to the resulting action that accounts for a variety of factors, including user preferences, properties of the device, and/or various factors related to the activity being controlled by the input device. For example, in the case where the input device is used to control a physical action, it may be useful for the mapping of user input to an activity controlled by the computing device so that the activity may be altered based on user preference, environmental factors, and/or characteristics of the user such as expertise and fatigue.

As used herein, the term "interaction behavior model" describes a model, algorithm, and/or other logic that may be used to customize display of information on a computing device, customize the display of information as a function of user input, and/or customize activity controlled by a computing device as a function of user input. An interaction behavior model may be used to control the speed of presentation of information presented by a computing device independent of the input device. In other embodiments, an interaction behavior model could be used to control how input devices result in actions performed by computing devices. In other embodiments, an interaction behavior model could be used to control how input from input devices is interpreted by computing devices. Interaction behavior models may access any number of inputs in order to determine how the computing device displays data and/or interacts with a user.

Various adjustments may be made by a computing system applying an interaction behavior model in response to user navigation input (e.g., via an input device). For example, adjustments may include:

Which image or portion of an image is displayed.

Image display characteristics such as brightness/contrast, window/level, magnification, panning.

Display parameters such as image view angle for computer generated 3D volumetric images and other renderings.

Spatial position and direction in 3D volumetric endoluminal fly through imaging as used in virtual colonography.

Parameters used in various types of image rendering, e.g., location and/or angle of a reconstruction plane in multiplanar reconstruction (MPR) and maximum intensity projection (MPR) reconstruction.

Spatial position and/or view angle in computer generated virtual environments.

In addition, an interaction behavior model could be used to control how user input via an input device is mapped into physical actions controlled by a computing device such as a machine or vehicle. For example, in various embodiments an interaction behavior model could be used to control how user input via a foot pedal or other input device controls the speed or steering of a car, boat, aircraft, spacecraft, submarine, robot or drone. Interaction behavior models may also be used in videogames and computer simulations, for example.

Example Factors

As noted above, various factors may be used by the computing device to customize operations performed by the computing device using an interaction behavior model, such as how the computing device responds to input received from one or more input devices from a particular user in a particular environment. For example, when a certain condition is met, e.g., one or more factors match a rule associated with a condition (see FIG. 5 and beyond), the effect of particular user inputs (e.g., movements of an input device) may be customized based on behaviors and/or modifiers associated with the condition. Thus, conditions may include any one or more thresholds of a factor (e.g., time of day is before 8 am or user has more than 10 years experience reading a particular exam type) and/or an indication of whether or not a factor is present (e.g., the image has not been previously viewed). Use of conditions that are based on various factors is discussed in further detail below.

Below are several factors that may be used in customizing interaction behavior models and/or selected parameters of interaction behavior models. Any one or more of these factors, and/or any other factors, may be used in customizing actions of a computing device in accordance with the systems and methods described herein.

Factors related to the user

Level of expertise, e.g., lower level of expertise may require longer viewing times of medical imaging exams Level of fatigue, e.g., number of hours worked that day, time of day, measures of user fatigue.

User preference.

Factors related to exam viewing

Complete read vs. viewing with a specific goal, e.g., a radiologist performing a diagnostic read on a brain MRI may prefer to view it at a slower rate than a neurosurgeon that has read the neuroradiologist's report and is primarily interested in the size and location of an intracranial hematoma for surgical decision making.

Viewing for complete read vs. for comparison purposes, e.g., a radiologist doing a primary interpretation of a chest CT may prefer to view it at a slower rate than a prior comparison exam that has already been interpreted.

Whether or not the current image has been viewed by the user. For example, one embodiment of an interaction behavior model might cap the image display rate at 5 images/second for unviewed images, but allow an image display rate of 20 images/second for images that have been viewed by the user.

Environmental factors

Room noise that could distract the user.

Ambient light that could make viewing of images more difficult.

Factors related to the display device

Spatial resolution.

Contrast resolution.

Background luminance and luminance range.

Brightness.

Characteristics of the Computing Device and Network

Bandwidth.

Bandwidth, e.g., a user may prefer a constant lower rate of image display than an irregular rate of display of sequential images that could be caused by a low bandwidth connection used to retrieve the images.

Computational speed.

Memory available for image preloading.

Factors related to the images being viewed

Image size in pixels (larger number of pixels may contain more information)

Signal to Noise Ratio (SNR)

The type of imaging exam being viewed, e.g., MRI, CT, nuclear medicine, etc.

Fraction of the image that is not homogeneous.

Factors related to the patient or other information related to the images

Clinical indication for the exam, such as evaluation of metastatic disease which may indicate that the probability of abnormalities is higher than a routine screening exam.

Prior exams. For example, in one embodiment, the interaction behavior model may be used to automatically slow the display rate of images in anatomic regions where abnormalities were identified on prior exams.

Computer Aided Diagnosis (CAD). For example, in one embodiment, the interaction behavior model may utilize CAD information or other forms of image analysis to slow display in regions flagged as suspicious. For example, CAD data indicating possible lesions in the liver may cause the interaction behavior model to slow down viewing of images including the liver, even if the user is providing the same input for proceeding through the images. For example, CAD data indicating possible lesions in virtual colonography may cause the interaction behavior model to slow down the rate of change of spatial position and direction in 3D volumetric endoluminal fly through imaging as used in virtual colonography.

Factors related to the way images are presented to the user

Image display size, e.g., larger size may require greater search time due to limited perceptual field of view.

Image display parameters, e.g., a greater fraction of an abdominal CT image may be relevant when displaying images with soft tissue windows compared to bone windows.

Use of image coupling where more than one image is changing on the screen, requiring the user to divide his attention between images Input device characteristics Precision with which the user can manipulate the display device, e.g., it can be difficult for users to precisely manipulate a joystick to a particular position but positioning it to within a range may be relatively easy The mapping of physical actions to computer behavior could be customized. For example, one user might prefer a forward tilt to increment image number while another might prefer the opposite. One user might want a forward tilt to navigate superiorly within the body regardless of how the patient was scanned.

Example Computing System

FIG. 1 is a system diagram which shows the various components of a system 100 for displaying information utilizing certain systems and methods described herein. As shown, the system 100 may include an information display computing device 150 (also referred to herein as a "computing device 150") and may include other systems, including those shown in FIG. 1.

The information display computing device 150 may take various forms. In one embodiment, the information display computing device 150 may be a computer workstation having information display modules 151. In other embodiments, modules 151 may reside on another computing device, such as a web server, and the user directly interacts with a second computing device that is connected to the web server via a computer network. The modules 151 will be described in detail below.

In one embodiment, the information display computing device 150 comprises a server, a desktop computer, a workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The information display computing device 150 may run an off-the-shelf operating system 154 such as a Windows, Linux, MacOS, Android, or iOS. The information display computing device 150 may also run a more specialized operating system which may be designed for the specific tasks performed by the computing device 150.

The information display computing device 150 may include one or more computing processors 152. The computer processors 152 may include central processing units (CPUs), and may further include dedicated processors such as graphics processor chips, or other specialized processors. The processors generally are used to execute computer instructions based on the information display software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The information display computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The information display computing device 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The information display computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The information display computing device 150 may also include one or more interfaces 157 which allow information exchange between information display computing device 150 and other computers and input/output devices using systems such as Ethernet, Wi-Fi, Bluetooth, as well as other wired and wireless data communications techniques.

The modules of the information display computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of information display computing device 150 may be combined into fewer components and modules or further separated into additional components and modules.

The information display computing device 150 may communicate and/or interface with other systems and/or devices. In one or more embodiments, the computing device 150 may be connected to a computer network 190. The computer network 190 may take various forms. It may include a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanners 120. The MRI scanner 120 may be used to acquire MRI images from patients, and may share the acquired images with other devices on the network 190. The network 190 may also include one or more CT scanners 122. The CT scanners 122 may also be used to acquire images and, like the MRI scanner 120, may then store those images and/or share those images with other devices via the network 190. Any other scanner or device capable of inputting or generating information that can be displayed as images or text could be included, including ultrasound, angiography, nuclear medicine, radiography, endoscopy, pathology, dermatology, etc.

Also connected to the network 190 may be a Picture Archiving and Communications System (PACS) 136 and PACS workstation 138.

Also connected to the network 190 may be an interaction behavior model data structure 160 used to store interaction behavior models. In various embodiments, the interaction behavior model data structure 160 may reside within PACS System 136, reside within a server accessible on a LAN that is local to the information display computing device 150, and/or reside within a server that is located remote to the information display computing device 150 and accessible via the Internet. In other embodiments, interaction behavior model data structure 160 may reside locally, within information display computing device 150. Interaction behavior model information may be stored in any computer readable format such as a database, flat file, table, or XML file, and may be stored on any computer readable medium, such as volatile or non-volatile memory, compact disc, digital video disc, flash drive, or any other tangible medium.

The PACS System 136 may be used for the storage, retrieval, distribution and presentation of images (such as those created and/or generated by the MRI scanner 120 and CT Scanner 122). The medical images may be stored in an independent format, an open source format, or some other proprietary format. One format for image storage in the PACS system is the Digital Imaging and Communications in Medicine (DICOM) format. The stored images may be transmitted digitally via the PACS system, often reducing or eliminating the need for manually creating, filing, or transporting film.

The network 190 may also be connected to a Radiology Information System (RIS) 140. The radiology information system 140 may be a computerized data storage system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a laboratory information system 144. Laboratory information system 144 may be a software system which stores information created or generated by clinical laboratories. Also attached to the network 190 may be a digital pathology system 146 used to digitally manage and store information related to medical pathology.

Also attached to the network 190 may be a computer aided diagnosis system (CAD) 148 used to analyze images. In one embodiment, the CAD 148 functionality may reside in a computing device separate from the information display computing device 150 while in another embodiment the CAD 148 functionality may reside within the information display computing device 150.

Also attached to the network 190 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D processing functionality may reside in a computing device separate from the information display computing device 150 while in another embodiment the 3D processing functionality may reside within the information display computing device 150

In other embodiments, other computing devices that store, provide, acquire, and/or otherwise manipulate medical data may also be coupled to the network 190 and may be in communication with one or more of the devices illustrated in FIG. 1, such as with the information display computing device 150.

As will be discussed in detail below, the information display computing device 150 may be configured to interface with various networked computing devices in order to provide efficient and useful review of medical examination data that is stored among the various systems present in the network. In other embodiments, information display computing device 150 may be used to display non-medical information.

Depending on the embodiment, the other devices illustrated in FIG. 1 may include some or all of the same components discussed above with reference to the information display computing device 150.

Input Devices

There are embodiments of the interaction behavior model in which the user controls presentation of visual information by interacting with an input device interfaced to an information display computing device. While embodiments will be described using input devices in which the user physically interacts with the input device, the systems and methods described herein can be applied to any input method including:

Devices that rely on direct physical interaction, including devices or portions of devices that the user rotates, tilts, presses, lifts up or down, squeezes, translates and/or touches, either with a body part or device such as a stylus.

Input methods that rely on measurement of a user's muscular or neural electrical activity.

Input methods that sense a user's position, configuration or motion, including body parts such as extremities, eyes, and face, for example using a video camera.

Input methods that rely on detection of sound, including recognition of voice commands.

Figure 2:
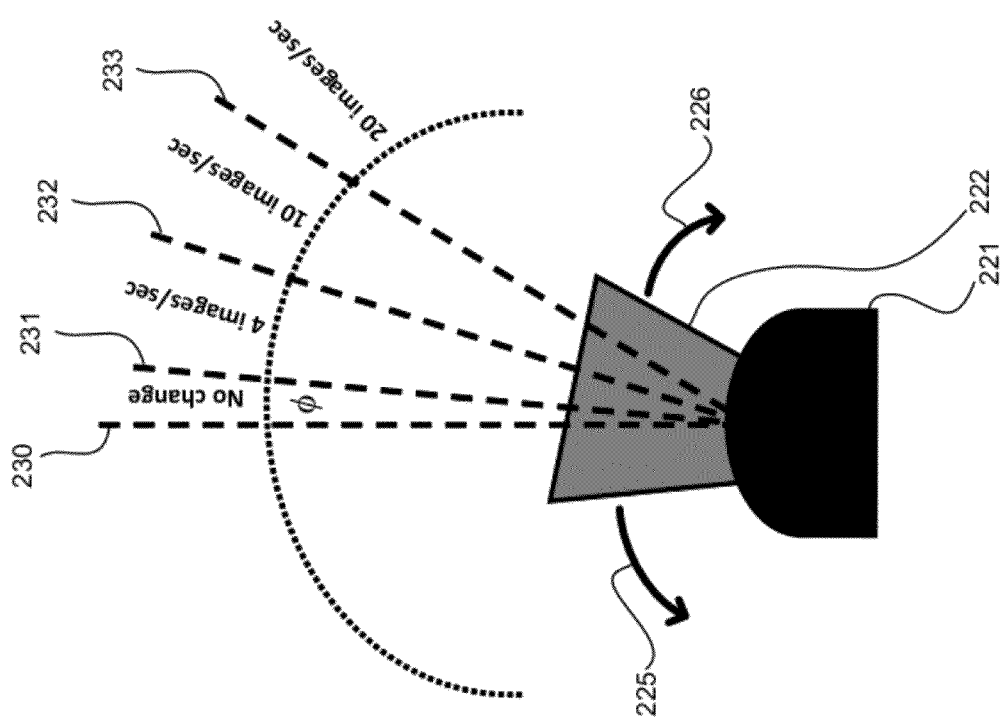
FIG. 2 illustrates an input device in which the user tilts a knob and the degree of the tilt is provided as input to a computing device.

FIG. 2 illustrates an input device 200 that utilizes input related to tilt. In this embodiment, the device illustrated has a base 221 and a knob 222 that is manipulated by the user. Knob 222 could instead be attached to something other than a base, such as a large input device, panel or dashboard. In this example, the user may tilt the knob to the left or right, illustrated by arrows 225 and 226, but in other embodiments the input device could accept user input in other ways, for example with translation, rotation, etc., as discussed below.

Figure 3:
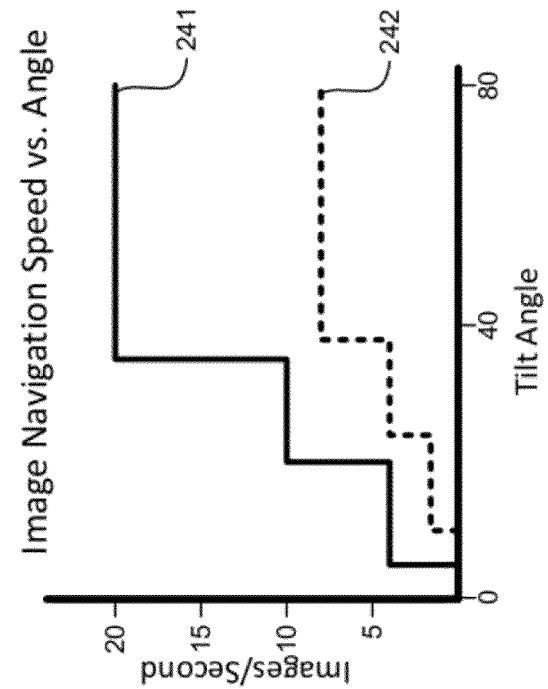
FIG. 3 is a graphical representation of information within an interaction behavior model, graphing the relationship between image navigation speed in images/second vs. the angle of tilt of an input device, such as the one shown in FIG. 2.

FIG. 3 is a graph illustrating image display rate verses tile angle of knob 222 with respect to base 221 (FIG. 2). In this embodiment, the information display computing device is configured to display a series of images at a rate that is controlled by the tilt that the user applies to the input device 200.

FIG. 2 and FIG. 3 illustrate changes in the display rate of images as the user tilts the knob 222 to the right. Although not illustrated, the same or different behavior might occur when the user tilts the knob 222 to the left. For example, tilting the knob 222 to the right of midline 230 might increment the number of the images displayed per second while tilting the knob to the left of midline might decrease the number of the images displayed per second, where the degree of tilt affects the rate of display of images. Thus, in this embodiment the degree of tilt off of midline determines the rate of display of images, while the direction of tilt determines a direction of movement within a series of images, such as whether the currently displayed image number should be increased (e.g., to move to a next image in an image series) or decreased (e.g., to move to a prior image in the image series). In other embodiments, other input device controls can be used in similar manners to determine the display rate of images and the direction of movement between images.

As illustrated in FIG. 2, the speed of image presentation would be determined by the degree of tilt from the midline 230 in FIG. 2. As illustrated in FIG. 2, a tilt between position 230 and 231 would result in no change in the image displayed. A tilt between position 231 and 232 would result in serial presentation of images at a rate of 4 images/second, between 232 and 233 a rate of 10 images/second, and beyond 233 a rate of 20 images/second.

The graph of FIG. 3 includes two different mappings between tilt angle and the action of the information display computing device. In particular, line 241 shows the mapping between tilt angle, shown on the horizontal axis, to image display rate, shown on the vertical axis. Line 242 shows another mapping in which the display rate is slower and the transition between display rates occurs at tilt angles that are different than those utilized within the mapping shown in line 241. In various embodiments, different mappings within an interaction behavior model might be chosen manually, for example as a user preference, or automatically, for example based on image size, image content, user fatigue, or other factors as discussed herein.

Figure 4:
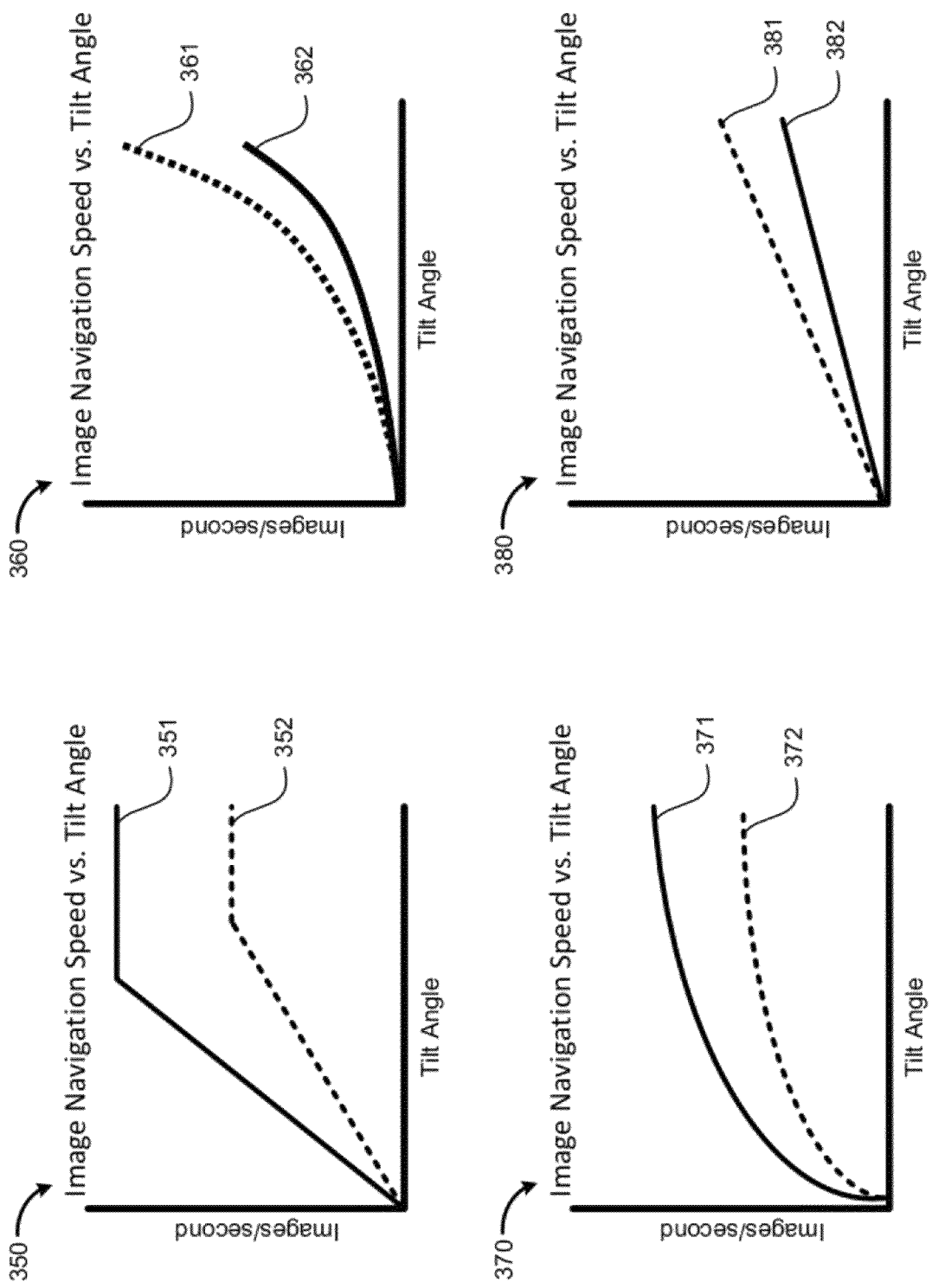
FIG. 4 shows examples of information within one or more interaction behavior models, mapping user input from an input device to the speed of image navigation on a computing device.

FIG. 4 illustrates four graphs that each illustrate exemplary mappings of image display rate as a function of tilt angle for a device such as the one shown in FIG. 2. In each of the mappings, illustrated by graphs 350, 360, 370, and 380, there are two lines illustrating different interaction behaviors that may be present in an interaction behavior model, but any number of behaviors may be present.

FIG. 5a shows another example of an embodiment of an interaction behavior model. In this case the information is represented as textual information rather than graphically as in FIG. 3 and FIG. 4. In this embodiment the interaction behavior model includes three components, behavior settings 390, modifier settings 392 and conditions 394. In this embodiment, the interaction behavior model defines two different behaviors B1 and B2 in the behavior settings 390. In this example, the behaviors B1 and B2 define rates of displaying images in response to a tilt angle of an input device. In other embodiments, behaviors may define any other display characteristic and/or feature in response to other defined inputs from one or more input device. In this example, the modifier settings 392 include four modifiers M1-M4 that may be applied to one of the behaviors B1 or B2 in response to meeting of certain of the conditions C1-C6 in the conditions settings 394. Thus, in one embodiment the conditions are rules that are applied to determine which of the behaviors should be applied and when the selected behavior should be modified by one of the modifiers. For example, condition C1 indicates that B1 is the default behavior. Thus, the display speed defined by B1 is used as a default when this interaction behavior model is selected. However, condition C2 indicates that if the exam from which images are displayed is a CTA exam, behavior B2 is to be used to define the display speed of images. Thus, the display speed may be changed based on the type of images that are displayed. Condition C3 indicates that a modifier (modifier M1) of the currently selected behavior (e.g., B1 by default or B2 if the exam is a CTA) to decrease the display rate by 20% is applied in response to display of an image that is greater than 1 megapixel. Accordingly, the behaviors may be modified in response to characteristics of the image being displayed. The remaining conditions in FIG. 5a illustrate other example criteria by which different behaviors may be selected and modifiers to the selected behaviors applied. In other embodiments, fewer, more or different components may be used.

Figure 5B:
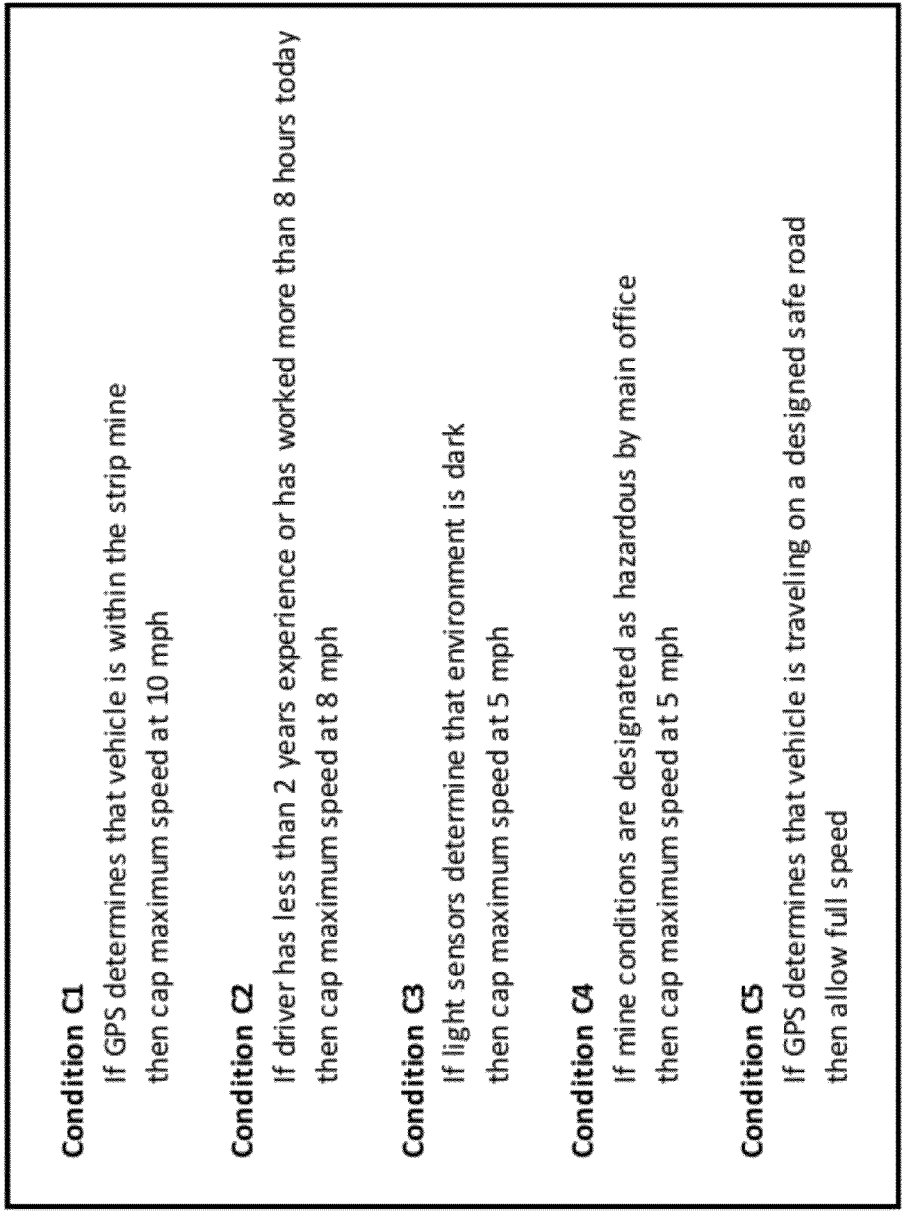
FIG. 5b illustrates information within an interaction behavior model.

FIG. 5b illustrates example conditions that may be used in an interaction behavior model that limits drive speed of a user operated vehicle. As noted above, interaction behavior models may be used in other contexts beyond image display. FIG. 5b illustrates one such example, but countless other uses of such interaction behavior models are within the scope of this disclosure.

In the example of FIG. 5b, conditions C1-C4 each cap the maximum speed of the vehicle to respective caps based on different criteria. In particular, condition C1 caps the speed at 10 mph if the GPS determines that the vehicle is at a particular location (e.g., a strip mine in the example of FIG. 5b), condition C2 caps the speed at 8 mph if the driver has less than 2 years experience or has worked more than 8 hours, condition C3 caps the speed at 5 mph if sensors determine that it is dark outside, and condition C4 caps the speed at 5 mph if the mine conditions are designated as dangerous, which may be determined based on a data structure that is updated to include such information in response to user and/or automated sensor input. Thus, the conditions of FIG. 5b are based on vehicle speed, user conditions and experience, environmental conditions, and current conditions defined by a third party. In other embodiments, any other criteria may be used to set maximum vehicle speed (or any other characteristic).

Figure 5C:
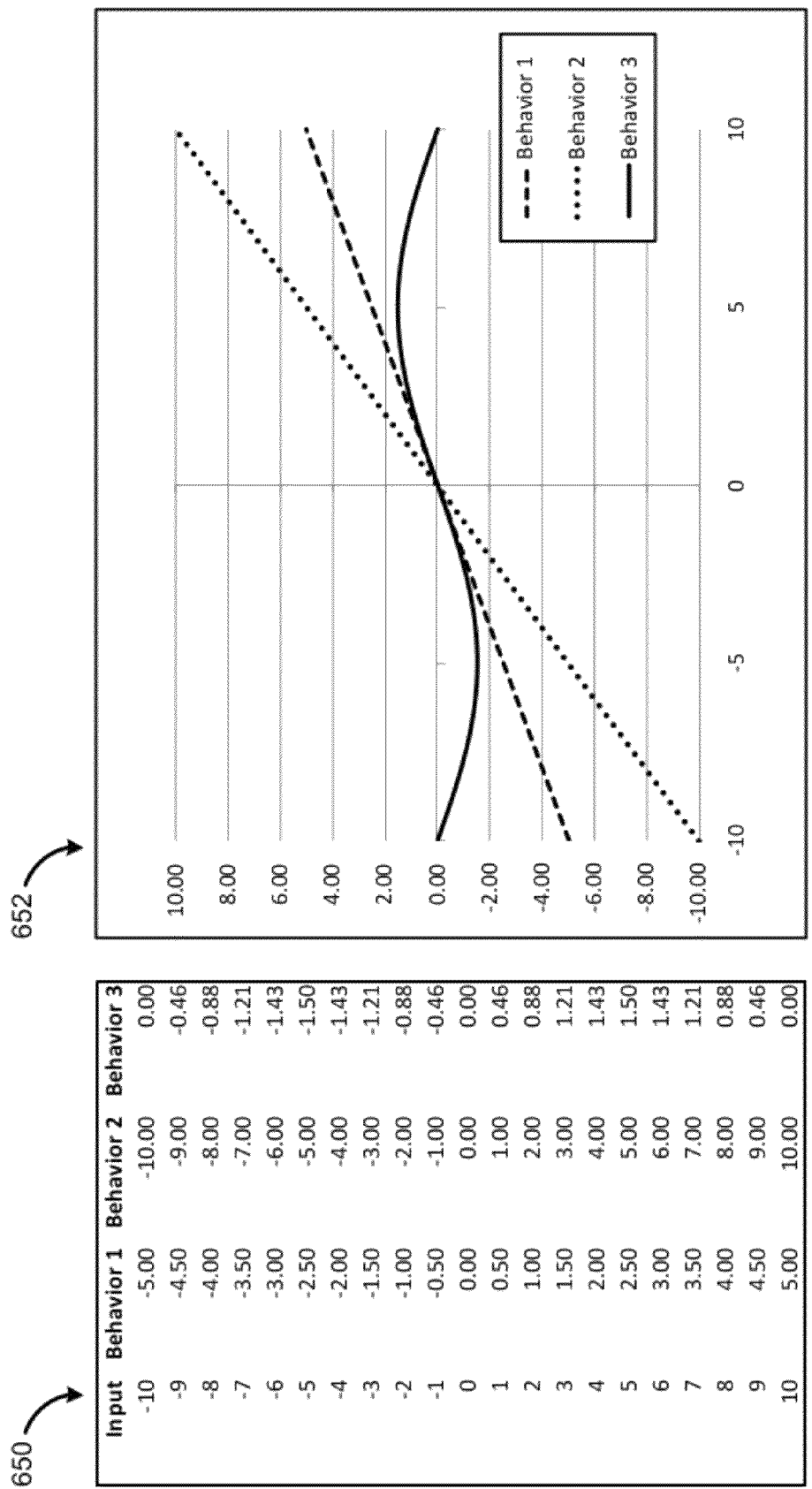
FIG. 5c illustrates an interaction behavior model that maps input to an output that can be interpreted by a computing device.

FIG. 5c illustrates sample data 650 and graph 652 that correlates input from an input device into various outputs that could be interpreted by a computing device. In this example, three associations between input and outputs are indicated as behavior 1, behavior 2, and behavior 3, illustrated in tabular form in data 650 and in graph 652. As described in other embodiments, the choice of which of the output behaviors is used could be based on one or more factors as described herein. In addition, these behaviors could be modified based on one or more factors as described herein.

Figure 6:
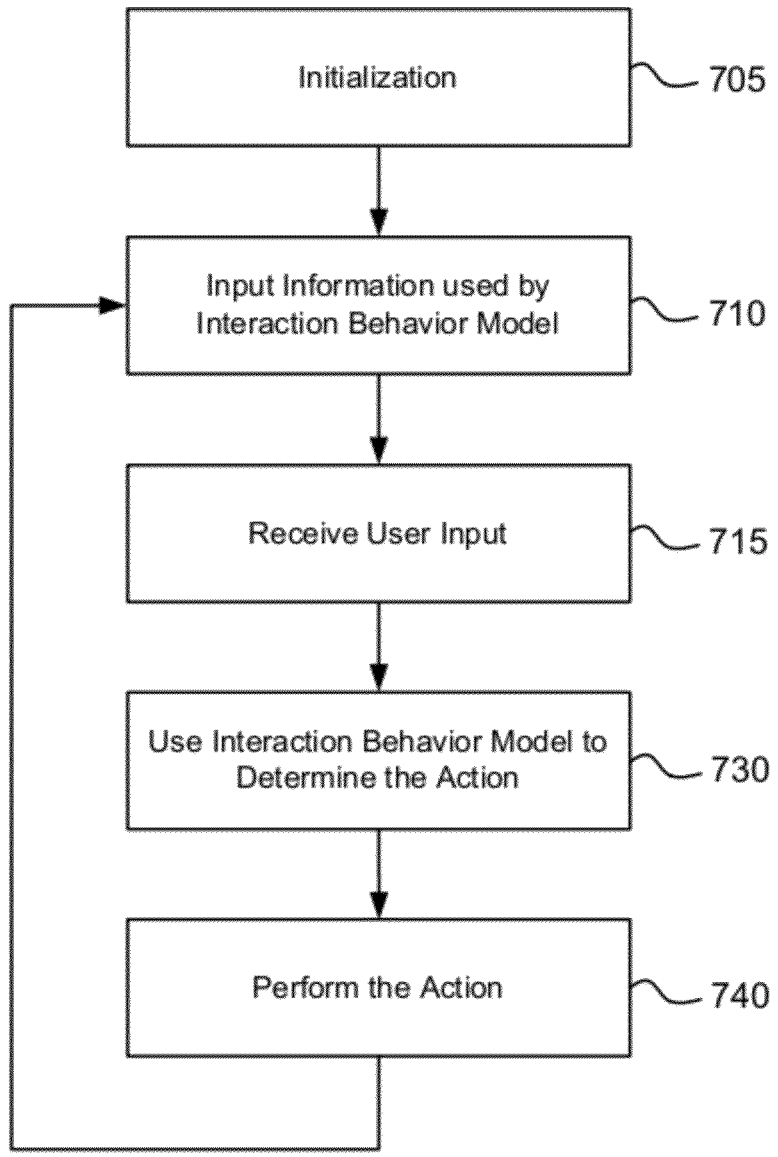
FIG. 6 is a block diagram depicting one embodiment of a system using the interaction behavior model.

FIG. 6 is a flowchart illustrating one embodiment of a method of implementing an interaction behavior model. In one embodiment, the method of FIG. 6 is performed by the information display computing device 150 of FIG. 1. For ease of explanation, the method of FIG. 6 is described herein with reference to the information display computing device 150, with the understanding that in other embodiments the method may be performed by any other suitable computing device. Depending on the embodiment, the flowchart of FIG. 6 may include additional or fewer blocks and/or the blocks may be performed in a different order than is illustrated.

At Initialization block 705, information relevant to the use of the interaction behavior model is accessed and/or retrieved, such as information regarding the user and his preferred interaction behavior model. For example, a particular user might prefer the interaction behavior model shown in FIG. 5a, while a different user might prefer a different interaction behavior model or a similar one with different default setting.

One or more interaction behavior models may be stored in interaction behavior model data structure 160 shown in FIG. 1 and/or stored, for example within information display computing device 150. User preferences could also be stored in interaction behavior model data structure 160 or in another data structure, for example within PACS System 136 of FIG. 1.

In other embodiments, there are no user specific preferences, but default interaction behavior models that could be determined by the manufacturer of the information display computing device or, for example, set by a site to apply to all users or to groups of users. For example, behavior B1 in behavior settings 390 (FIG. 5a) might be applied as the default behavior to radiologists in training at a site while behavior B2 might be applied by default to staff radiologists.

In block 710, with a behavior selected (e.g., based on conditions, such as conditions 394 of FIG. 5a), the computing system determines if any modifiers should be applied to the selected behavior and/or if a different behavior should be selected. In the example of FIG. 5a, this is done via the conditions C2-C6, which indicate application of modifiers and/or changes to the current behavior in response to the indicated conditions. Using the conditions of FIG. 5a, for example, if the patient has cancer or is suspected of having cancer, condition C6 (section 394 in FIG. 5a) would result in the application of modifier M2 which would slow the image display rate by 50%. Behaviors may be selected and/or customized based on any one or more of the factors listed above and/or any other factors, and may be applied using a condition/rule system such as in FIG. 5a, or in other manners.

While some factors such as clinical information may not change during the course of viewing the imaging exam, other factors may change dynamically, such as:
  The size of the image being displayed (relevant to condition C3 in the example illustrated in FIG. 5a).
  Whether a nearby image has been marked as positive by a Computer Aided Detection (CAD) system (relevant to condition C4 in the example illustrated in FIG. 5a).
  Image display parameters (relevant to condition C5 in the example illustrated in FIG. 5a).

Thus, in some embodiments the behavior and/or modifiers to behaviors are adjusted in real time as a user views medical images. For example, if a user initially views images that are less than 1 megapixel, condition C3 is not triggered, but if the user moves to an image in an image series or otherwise displays an image that is 1.1 megapixel, condition C3 may be immediately triggered such that the image is displayed with modifier M1 applied. Information regarding any other factors may be accessed and/or retrieved in block 710, such as the factors listed above and/or any other factors.

In block 715 user input is received via any available input devices and/or user interactions. For example, in the embodiment of FIG. 2, user input would include the tilt angle the user has applied to knob 222 and may include other input, for example from a keyboard, mouse, or other buttons on the input device with the tilt knob illustrated in FIG. 2. As noted above, the input device of FIG. 2 is provided only as an example of an input device—any other input device, even an input device that doesn't require direct user contact, such as a motion detection camera or microphone, may be used in place of the tilt knob.

In block 730, the information display computing device 150 applies the selected interaction behavior model, including any modifications, in order to determine the appropriate action. For example, in the embodiment of FIG. 5a this may be accomplished by applying the conditions sequentially to determine the behavior and any modifiers that would be mapped to the received user input. For example, consider an MRI of the Brain in a patient with a clinical history of Lung Cancer when the user is applying a tilt angle of 11 degrees to the knob of the input device illustrated in FIG. 2. Stepping through the conditions sequentially in the example illustrated in FIG. 5a:
  Condition C1 is always applied initially so behavior B1 is initially selected.
  Condition C2 is false as the exam is an MRI not a CTA, so behavior B2 is still selected.
  Condition C3 is false as the MRI images are <1 megapixel/image.
  Condition C4 is false as CAD was not utilized.
  Condition C5 is false as the modality is not CT.

Condition C6 is true as the history is cancer so Modifier M2 is applied to the current selected behavior B1.

Having stepped through the conditions in this example, the information display computing device 150 would determine that behavior B1 with modifier M2 are to be applied to the received user input. Applying a tilt angle of 11 degrees to behavior B1 maps to a display rate of 10 images/sec. Applying modifier M2 (activated by condition C6) decreases the display rate by 50%, resulting in a display rate of 5 images/second.

In block 740 the determined action is performed. In this example, the information display computing device 150 also considers the direction of the tilt of knob 226, left vs. right, to determine whether the image to be displayed within the series is to be incremented or decremented. Assuming the knob is tilted to the right, the image number within the series is incremented and the resulting image is displayed for 200 milliseconds, the determined rate of 5 images/second before a new image is displayed. The logic loops back to block 710 to repeat the process.

In other embodiments the user has the option of overriding the interaction behavior model, for example by pressing a key that returns to the default behavior.

Image Navigation Using Other Input Devices

With the device shown in FIG. 2, the input device senses the degree of tilt of a knob manipulated by the user. Tilt input could also be sensed in other ways, for example by devices that utilize accelerometers, including handheld controllers such as the Wiimote made by Nintendo, and computing devices with internal sensors such as the iPhone and iPad made by Apple. However, other technology, including cameras and other sensors, may be used to sense the physical positions of objects or body parts. The embodiments described herein may be used with any devices and/or methods that are capable of sensing the desired user input, such as tilt in the embodiment of FIG. 2.

Figure 7:
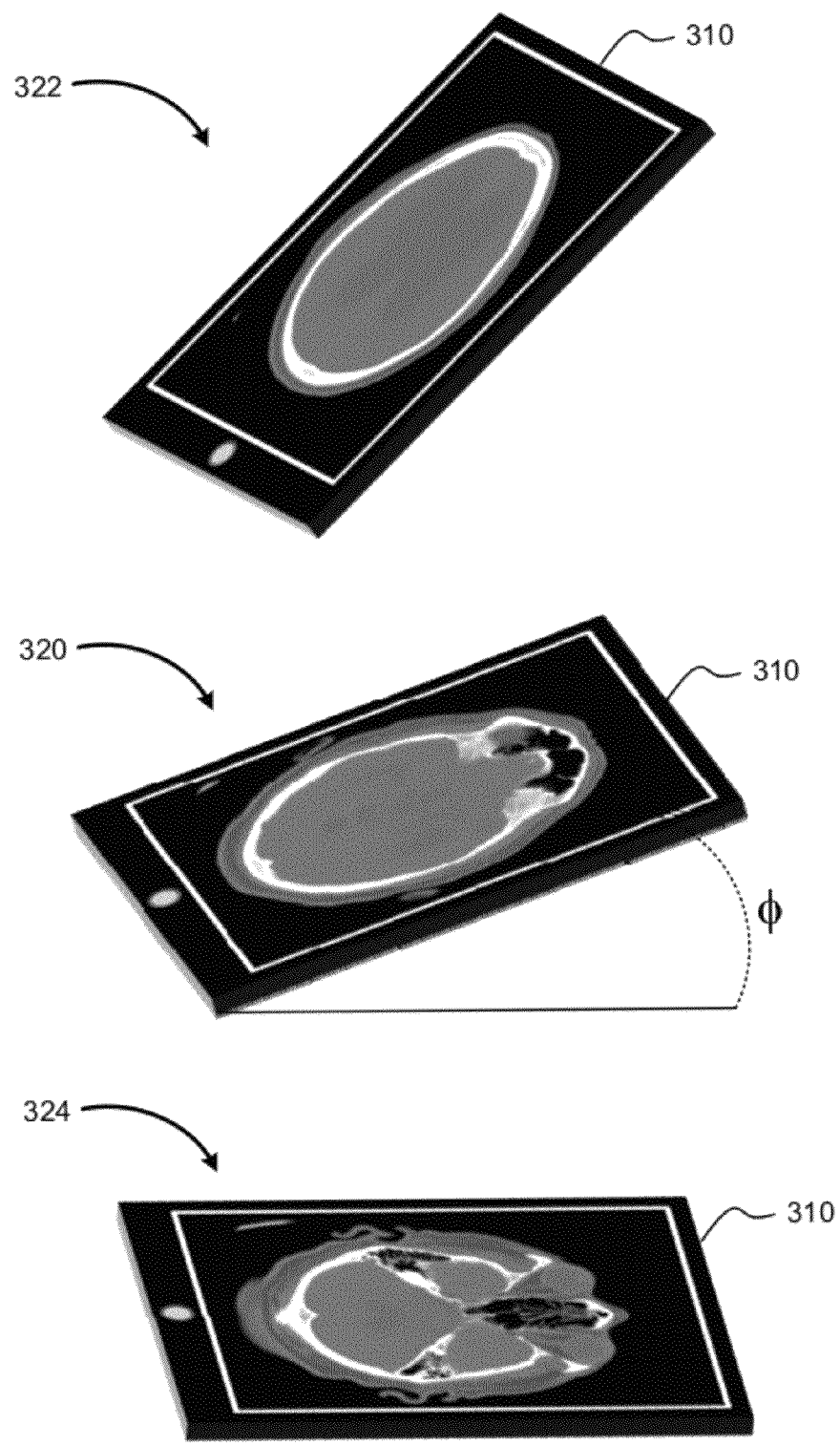
FIG. 7 illustrates a computing device with a display screen and a sensor that detects the tilt of the device and depicts how the device can be tilted by the user to provide input using an embodiment of the interaction behavior model.

FIG. 7 illustrates a device 310 that includes a display screen and a sensor that detects the device orientation. By tilting the device, the user can provide tilt information to the device in a way that is analogous to tilting the knob in the input device illustrated in FIG. 2.

In view 320 of FIG. 7, device 310 is shown in a particular position, theta degrees from horizontal. In one embodiment, the user may indicate to the computing device that the current tilt of device 310 is to be assigned as a neutral position, for example by pressing a button on the device or touching a control on the touch screen. When in this neutral position, the computing device would not change images, which is analogous to a midline position of the knob in FIG. 2. Tilting device 320 to angles different than theta, such as is shown in views 322 and 324, would be similar to tilting the knob of the device shown in FIG. 2. For example, tilting the device 310 into positions 322 or 324 may be equivalent to tilting the knob of the device shown in FIG. 2 to the left or the right, respectively, causing an increase or decrease in the number of the image displayed within the series, where the degree of tilt from the neutral position may determine the rate of incremental image change, as described previously.

In another embodiment, the actual tilt may be mapped to different images in the series. For example, in a series with 90 images, positioning the device horizontally, such as shown in view 324, may cause display of image 1, and positioning the device vertically might cause display of image 90, with intermediate angles causing display of intermediate images in a linear fashion.

In other embodiments the interaction behavior model may be used with left and right tilting of the device 310. In other embodiments, other input devices that are manipulated in other ways, for example as illustrated in FIG. 8, may be used in conjunction with interaction behavior models.

Figure 8:
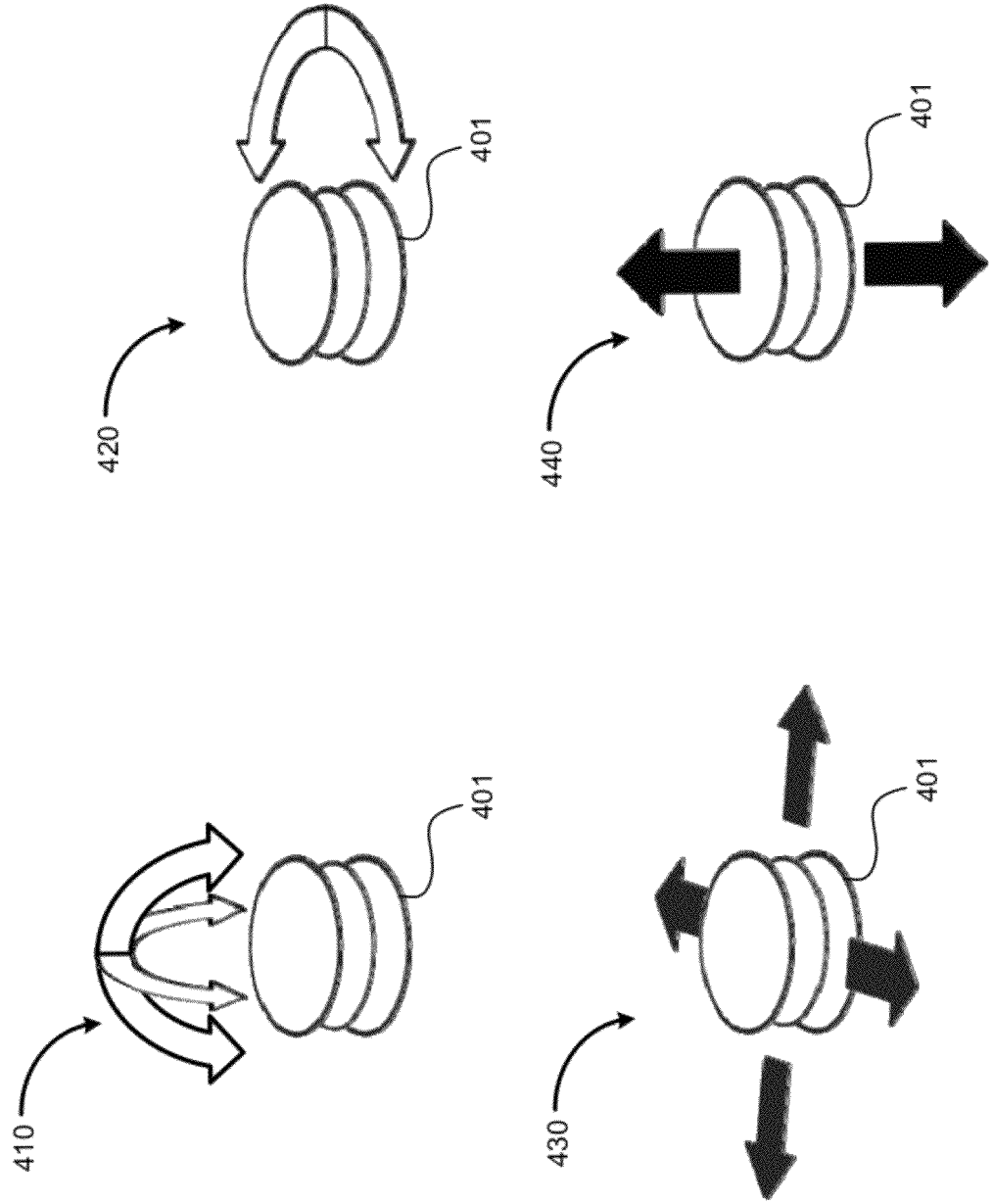
FIG. 8 shows different modes of user input, tilting, rotation, and translation.

FIG. 8 illustrates another example input device, in particular, a knob 401. In view 410 of FIG. 8, knob 401 of an input device may be tilted left-right and/or forward-backward, as illustrated by the curved arrows above the knob 401. The systems and methods described herein may be applied to one or both of these two axes of tilt.

In view 420, a different input mode is shown, where the knob 401 may be twisted clockwise and counterclockwise, where the twisting motion may be independent from the motions shown in view 410. The systems and methods described herein may be applied to rotation, where angle or rotation is treated in a way that is similar to angle of tilt, as previously described.

In view 430, the knob 401 may be translated by the user forward-backward and/or left-right. The systems and methods described here may be applied to these directions as well.

In view 440, the knob 401 may be translated by the user superiorly/inferiorly, perpendicular to the direction of translation shown in view 430. This systems and methods described herein may be applied to this input mode as well.

In the device's shown in FIG. 8, as the user translates, tilts, and/or rotates the knob of the input device from a neutral position to change the angle of tilt, angle of rotation, and/or degree of translation, the direction, timing, and/or other factors of image viewing (or other computer functionality) may be adjusted according to an interaction behavior model. Depending on the embodiment, the input device may include one or a combination of multiple of the movement capabilities discussed with reference to knob 401.

Figure 9:
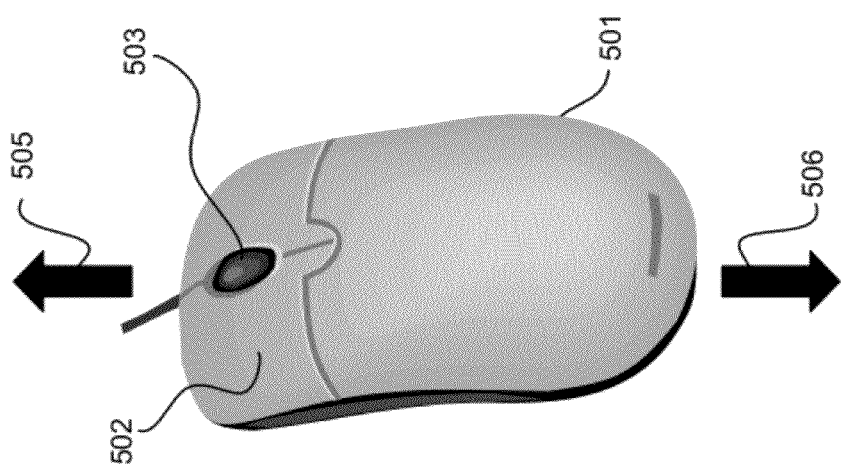
FIG. 9 illustrates a mouse that includes two buttons and wheel.

FIG. 9 illustrates movements of a mouse 501 that can be used to control a user interface for viewing images. In one embodiment, the user holds down a button 502 on the mouse 501 and moves the mouse 501 forward (motion indicated by arrow 505) or backward (motion indicated by arrow 506) on a surface to cause images to change. Typically a fixed increment in physical mouse position results in a fixed change in the number of the image displayed. For example, forward motion of 2 mm might result in an increase in image number and backward motion of 2 mm might result in a decrement in image number. Movement of a mouse wheel 503 may provide similar inputs that are usable to provide image navigation commands.

Figure 10:
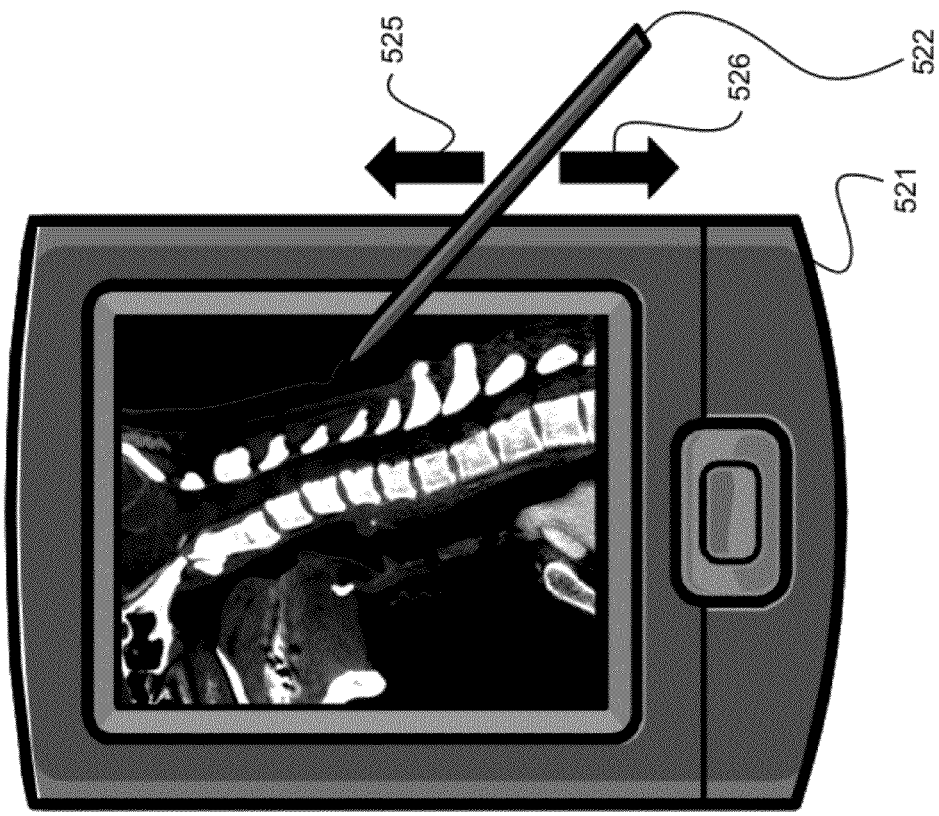
FIG. 10 illustrates a handheld computing device such as a smartphone, PDA or tablet computer that includes a touch screen.
Figure 11:
FIG. 11 illustrates a user interacting with a tablet computer or display with a touch screen.

Another system that may make use of interaction behavior models might be a touch screen that is separate or integrated with a display device. For example, FIG. 10 illustrates a handheld computing device 521 and FIG. 11 illustrates a larger tablet computer 601 with an integrated display and touchpad. With reference to FIG. 10, a stylus 522 may be moved in the directions illustrated by arrows 525 and 526 in order to navigate between images. Similarly, a finger could be utilized instead of a stylus, for example in the case of a smartphone or the tablet computer 601.

As illustrated in FIGS. 9, 10 and 11, a user can move the mouse 501, roll the mouse wheel 503, move a trackball, or move a stylus or finger on the touchpad of device 521 or device 601 in order to provide user input that could be mapped by an interaction behavior model, for example to navigate through images, where an incremental change in the degree of rotation of a trackball or incremental movement of the mouse position or a finger or stylus on a touch screen causes the information display computing device to change the image displayed (and/or other display characteristics, such as speed of changing between images).

Figure 12:
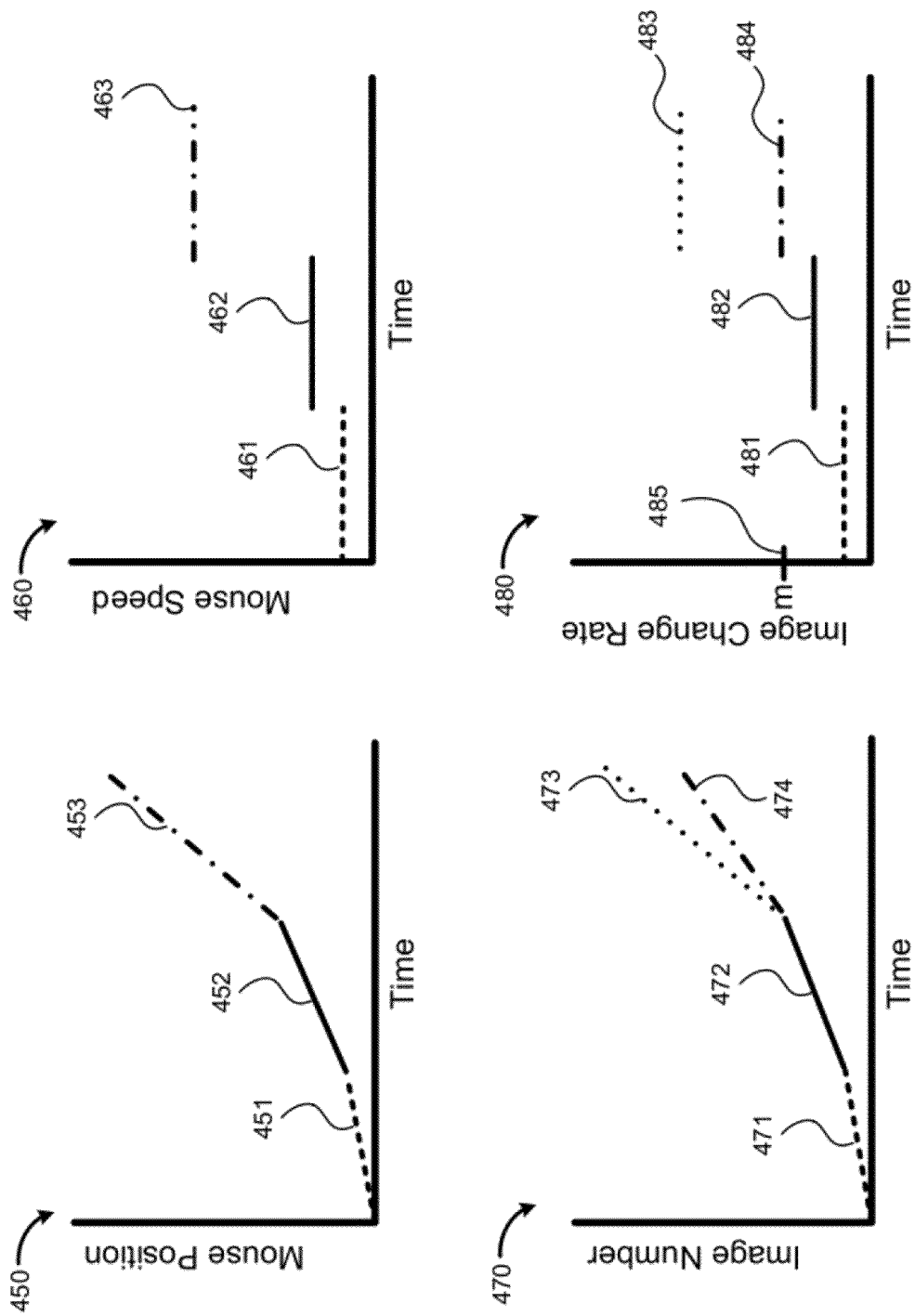
FIG. 12 illustrates one embodiment of an interaction behavior model that may be used to implement certain systems and methods described herein.

FIG. 12 illustrates four graphs 450, 460, 470, 480 that illustrate inputs and outputs of an interaction behavior model over time. In particular, FIG. 12 illustrates mouse position in graph 450, mouse speed in graph 460, image number in graph 470, and image change rate in graph 480, each with reference to a common time period and user interaction with the mouse. Graph 450 shows an example of mouse position over time, for example along the direction of movement indicated by arrow 505 of FIG. 9. In this example, the user moves the mouse forward first at a slow rate (segment 451), then a medium rate (segment 452) and finally at a fast rate (segment 453). The rate of movement for these three time periods is shown in view 460, as mouse speeds 461, 462, and 463.

The line segments 471, 472, and 473 in the graph shown in graph 470 indicate the number of the image that would be displayed from a series of images as a function of time as a result of the mouse movement graphed in view 450, where a fixed incremental movement of mouse position results in a fixed incremental change in image number. The rate of change of image number that corresponds to the image number graph 470 shown in the graph 480, where image change rate 481 corresponds to segment 471, image change rate 482 corresponds to segment 472, and image change rate 483 corresponds to segments 473.

In one embodiment, an interaction behavior model may be applied to cap the maximum rate of image change, illustrated in the graph 480 by the "m" on the vertical axis. For example, a behavior and/or a modifier may be defined that sets a maximum image change rate to m. Therefore, the image change rate 483 would be reduced to the image change rate 484 (which is equivalent to m). This would result in a change in the image number over time illustrated in the graph of view 470, where the third segment of the graph would be segment 474 rather than segment 473.

While the embodiment of FIG. 12 was described using incremental movement of a mouse, in other embodiments other input devices could be used including input on a tablet by finger or stylus, rotation of a trackball, rotation of a mouse wheel or knob, and other input devices that sense change in position or orientation.

In one embodiment, an input device, such as a joystick, may be used to provide commands. A joystick, or other device wherein movement returns to an original home position when the user releases the device, may be used in a similar manner as discussed above with interaction behavior models. Such devices may detect one or more of tilt, translation, and/or rotation of the joystick.

Example Digital Pathology

Figure 14:
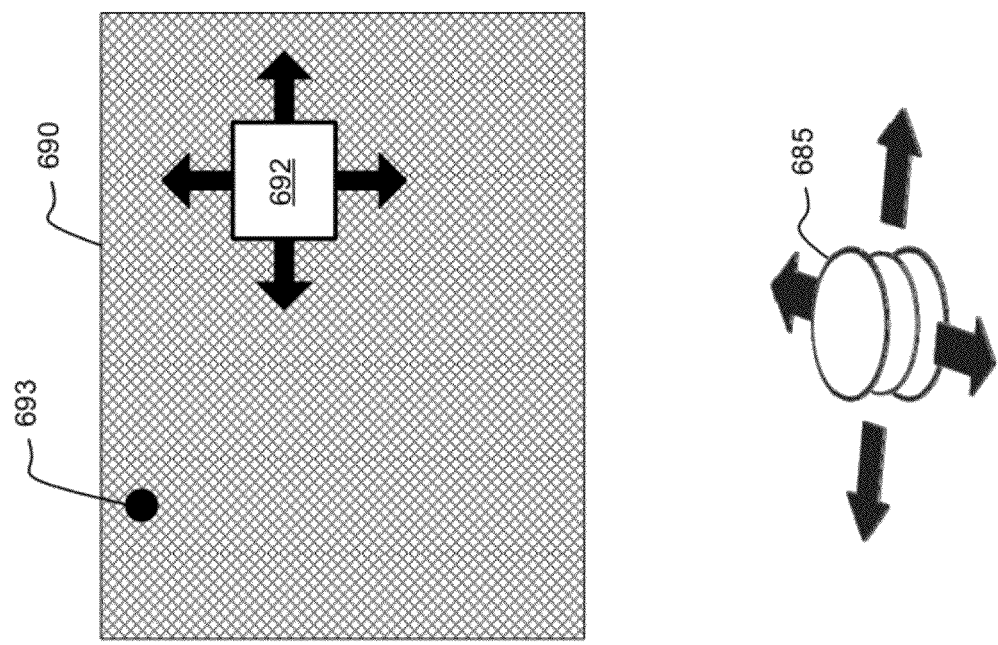
FIG. 14 shows aspects of an embodiment of an interaction behavior model used with digital pathology.
Figure 14:
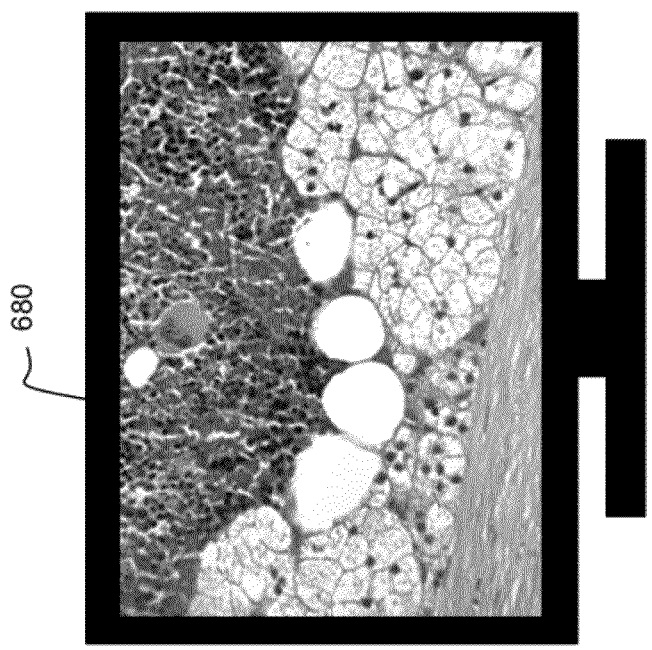

FIG. 14 illustrates computer monitor 680 displaying a pathology image, for example from a Pathology Information System. Such a pathology image may be much larger than can be displayed at full resolution on a computer monitor. For example, a digital pathology image as might be acquired using a digital slide scanner, represented by image 690, might be 100,000×100,000 pixels in size. However, the display resolution of a computer monitor, represented by monitor 680, might be on the order of 1,000×1,000 pixels.

If pathology image 690 is to be displayed at full resolution on monitor 690, only a fraction of image 690 may be displayed at any one time. Rectangle 692 represents that portion of image 690 displayed on monitor 680, a viewport into the image. The portion being viewed may be changed interactively by the user, represented by the black arrows along the sides of viewport 692.

In one embodiment, the user utilizes a knob 685 (or any other input device), shown with four black arrows indicating that the user can translate the knob. When the computing device senses translation of input device 685, that input is used to translate the position of viewport 692 into image 690, allowing the user to interactively display different portions of image 690.

Just as it is possible for users to display images at rates that exceed their perceptual ability to accurately interpret them, it would be possible for a user to translate the monitor viewport 692 at rates that exceed his ability to accurately interpret the information being displayed on monitor 680. Therefore, the systems and methods described herein may be used to map the input from the user input device 685 into the speed of translation of viewport 692.

In other embodiments, other input device modes, such as the up-down translation shown in view 440 of FIG. 8, may be used to change the magnification of the image displayed on monitor 680. This allows pan and zoom of an image to be controlled by a single input device, with up-down translation controlling zoom and left-right/forward-backward translation controlling pan.

There are many fields where image size exceeds the display resolution of the computing device and in other embodiments, other types of images may be used, such as satellite imagery, telescope imagery, seismic imagery, and mammography.

Example 3D and Image Rendering

In medical imaging and other areas imaging data may be processed to produce 3D or other rendered images. In medical imaging, imaging information may be processed to create 2D images that are at planes other than the plane in which the images were acquired. Volumetrically acquired imaging information, for example with CT, MRI and ultrasound, may be processed to create 2D or 3D images, including 3D volume rendering, surface rendering, multiplanar reformatted images (MPR), and maximum intensity projection (MIP) images. In some cases, 3D volume rendered images may be used to visualize the internal surfaces of structures, such as endoluminal imaging of the GI tract with CT colonography as well as endoluminal imaging of airways, vessels and other structures.

Embodiments described herein may be used with these and/or other types of images. For example, the speed with which a user travels through a 3D volume rendered structure, such as the inside of the colon with CT colonography, may be controlled with the illustrative systems and methods described herein. For example, the speed with which a user traverses images of a colon may be modified as a function of the user's expertise, the roughness of the internal surface of the colon, and/or the presence of regions marked as suspicious or abnormal by a computer aided diagnosis system (CAD) as discussed below.

Example Computer Aided Diagnosis (CAD)

Imaging information may be analyzed by computers to detect regions of interest. In medical imaging this is known as Computer Aided Diagnosis (CAD). Examples include the detection of cancers in mammograms, detection of lung nodules in chest CT, detection of polyps in CT colonography, and detection of abnormal cells in pap smears.

Generally, CAD systems are not sufficiently accurate to make a final diagnosis, but rather detect suspicious areas for further scrutiny by the expert human reader. Marks of some sort may be superimposed on the images to indicate to the human reader the regions marked as suspicious by the CAD system. These marks could be placed at the suspicious locations in the originally acquired images, for example in mammography, or rendered images, for example 3D or MPR images in the case of CT colonography.

In one embodiment, an interaction behavior model may be used with CAD to modify the display of various types of visual information. For example, in the case of a user viewing a series of 2D images such as a chest CT, the rate of image display could be slowed in the regions marked by CAD, whether or not marks are displayed on the images to indicate the regions marked by CAD. For example, in a series of images, the maximum image display rate could be cut by 50% (e.g., and/or required magnification level, contrast level, etc.) for images within 10 mm of an image that has one or more regions within it marked by CAD. Depending on the embodiment, such changes in display rate might be expressed in modifiers that are responsive to the indications conditions in an interaction behavior model. In another example, the maximum image display rate could be modified as a result of an interaction behavior model for images within a certain distance of a region marked by CAD, regardless of the image's 3D spatial orientation.

Figure 15B:
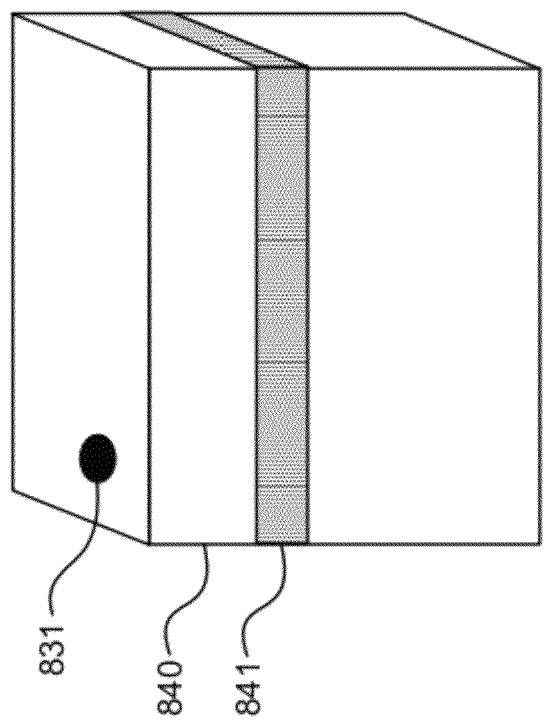
FIG. 15b shows aspects of embodiments of an interaction behavior model in which a region of an imaging volume have been marked by CAD.
Figure 15A:
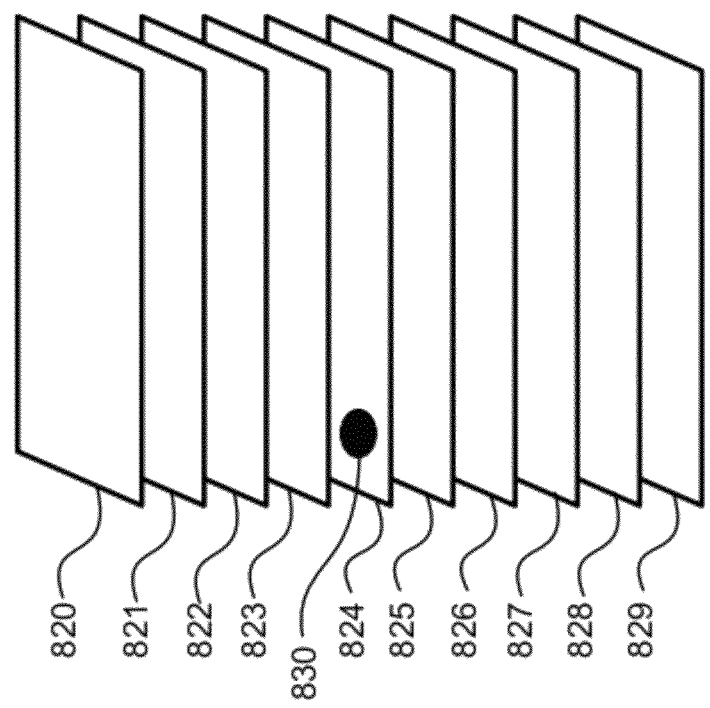
FIG. 15a shows aspects of embodiments of an interaction behavior model in which a region of an image has been marked by CAD.

FIG. 15a illustrates a series of images 820-829, each representing a plane of imaging through a region of anatomy. The thickness of the anatomy depicted in images could vary, from contiguous slices (no gap between the slices), to slices that overlap, to slices having a gap between the images. For the purpose of illustration, image 824 is shown with an associated CAD marker 830. By way of example, images might be acquired at 1 mm intervals and an interaction behavior model might be selected (and or modified by one or more modifiers) to:

Cap the display rate at 2 images/second for images within 2 mm of a slice with a CAD mark.
Display images with a CAD mark for a minimum of 1 second.

With this example behavior and assuming 1 mm slice spacing, display of images 822, 823, 825 and 826 would be capped at a display rate of 2 images/second and image 824 would be displayed for a minimum of 1 second when the user displayed those images.

Figure 16:
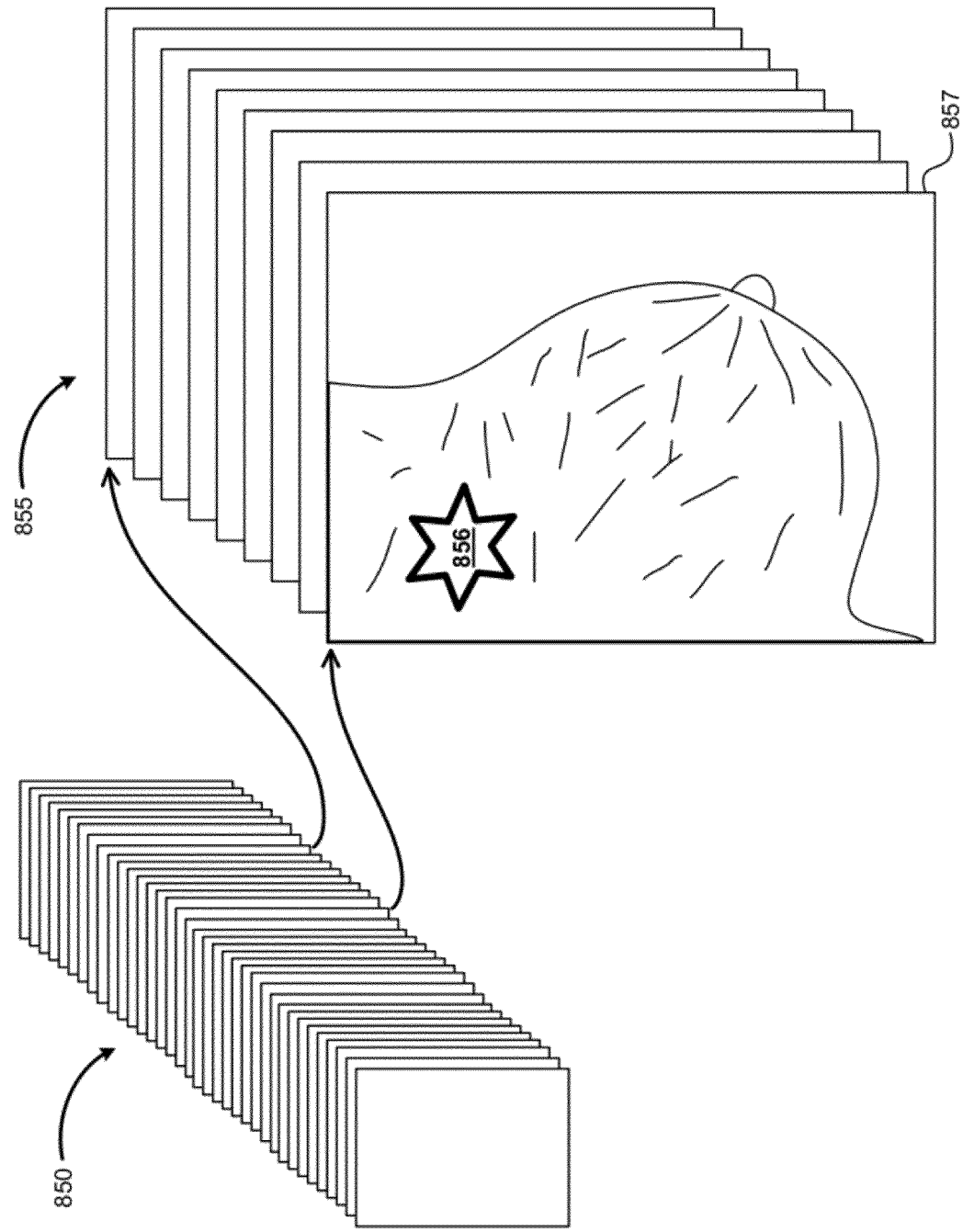
FIG. 16 shows aspects of an embodiment of an interaction behavior model in which a region of a mammo tomosynthesis exam has been marked by CAD.

An embodiment of an interaction behavior model may be used in mammo tomosynthesis, as illustrated in FIG. 16. FIG. 16 illustrates a series of images 850 of different positions of a breast, and a larger view of a subset 855 of those images. Marker 856 is displayed by the computing device and indicates a location marked as suspicious by CAD within image 857. As discussed above, an embodiment of the interaction behavior model may be configured to alter the display of images in proximity to images marked by CAD, in this example image 857. By way of example, images in the exam that are within a 10 mm distance from an image marked by CAD, image 857 in this example, might be displayed for a minimum of 2 seconds. In other embodiments, the minimum display time or maximum image display rate might be applied only to these images when they are displayed for the first time to the user. In other embodiments, other characteristics of image display might be changed for images in proximity to images with CAD markers, e.g., magnification, color mapping, brightness, and/or contrast. Other embodiments can also be applied to other types of imaging where CAD may be utilized, e.g., breast MRI, chest CT, and/or CT colonography.

In the case of reformatted images, for example thick-slice MIP applied to chest CT, an embodiment may be used to control the rate of movement of the plane of reconstruction through the imaging volume. For example, the rate of movement of the plane in mm/sec could be capped at 5 mm/second when the reconstruction plane is within 20 mm of a region in the imaging volume marked by CAD.

FIG. 15b shows aspects of embodiments of an interaction behavior model in which a region of an imaging volume has been marked by CAD. For example, a CAD marker 831 is shown in a spatial position within the superior aspect of the imaging volume 840. A slab of the imaging volume being reconstructed by thick-slice MIP or another technique is shown as shaded volume 841. For the example above, the speed that the user could move the location of reconstruction slab 841 would be capped at 5 mm/second when the reconstruction slab was within 20 mm of the region marked by CAD, in this example region 831.

In the case of 3D volume rendering, for example, endoluminal imaging such as CT colonography, an embodiment may be used to control visual display and 3D rendering. For example, CAD may be used to mark suspicious regions on the inner surface of the colon and it is important that the user be aware of these regions. In one embodiment, the rate that the user traverses the colon via endoluminal 3D volume rendering may be automatically controlled by the presence of CAD markers or locations marked as suspicious by CAD, whether or not markers are displayed, for example slowing the rate of "movement" when the region being viewed is in proximity to a CAD mark. It is possible for an area of interest marked by CAD to be hidden from view because of the complexity of the inner surface of the colon, for example requiring the user to look sideways or backwards. In one example, the user is not permitted to move further than 2 cm beyond the CAD mark until that region marked has been displayed on the computer device. This may require the user to change his view within the colon so that he "looks" sideways or backwards.

In another embodiment, interaction behavior related to image translation might be controlled by the presence of CAD markers. In the example embodiments described above with reference to FIG. 14, an image 690 could have a CAD marker 693. The rate of translation of viewport 692 could be automatically slowed when it is in the proximity of CAD marker 693. In other embodiments, a reader could not terminate viewing of image 690 until all CAD markers were viewed.

Example Control of Machines

In other embodiments, the interaction behavior model may be used to control how user input via an input device is mapped into physical actions controlled by a computing device such as a machine or vehicle, rather than display of information. For example, in various embodiments the interaction behavior model could be used to control how user input via a foot pedal or other input device controls a car, boat, aircraft, spacecraft, submarine, robot or drone.

For example, FIG. 5b is an embodiment of an interaction behavior model that could be used to control the behavior of a strip mining truck's speed as a function of user input and several conditions. In this example, the maximum speed of the truck is modified based on a number of factors including the physical location of the truck, the experience of the driver, the potential for driver fatigue based on number of hours worked that day, and environmental conditions.

Summary

All of the methods and processes described above may be embodied in, and partially or fully automated via, software code modules executed by one or more general purpose computers. For example, the methods described herein may be performed by an information display computing device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

While the methods described herein are typically implemented as software modules, they may alternatively be embodied in specialized computer hardware or firmware. For example, certain methods, portions of methods, and/or combinations of methods may be implemented in hardware modules comprising programmable units, such as programmable gate arrays (e.g., FPGAs) or application specific integrated circuits (e.g., ASICs). The results of the disclosed methods may be stored in any tangible computer readable medium.

What is claimed is:

1. A computing system comprising:
   one or more hardware processors configured to execute software instructions stored in modules; and
   a tangible computer readable medium storing modules configured for execution by the one or more hardware processors, the modules configured to:
      access a data structure storing conditions associated with respective behavior models, each of the behavior models indicating associations between two or more rates of display of medical images and a corresponding two or more levels of interaction, each of the two or more levels of interaction indicated by movements of an input device of the computing system;
      select a behavior model based on one or more characteristics of:
         the computing system, an environment surrounding the computing system, the display device, bandwidth available to the computing system, the medical images, a patient, a medical history of the patient, and/or an input device; and
      in response to a first movement of the input device indicating a first level of interaction:
         determine a first rate of display of medical images based on an association between the first level of interaction and one of the two or more rates of display of medical images in the selected behavior model.

2. The computing system of claim 1, wherein the modules are further configured to:
   identify one or more modifications that are matched by one or more characteristics, wherein one or more of the identified modifications indicate an adjustment to the determined first rate of display of medical images, wherein the determined first rate at which the medical images are displayed is modified by the adjustment.

3. The computing system of claim 2, wherein the adjustment indicates a percentage increase or decrease or an absolute time period.

4. The computing system of claim 2, wherein one or more of the identified modifications include a maximum rate at which the medical images are displayed.

5. The computing system of claim 1, wherein the level of interaction is determined based on one or more of an angle of a knob of the input device with reference to a neutral position; a pressure applied, a speed of movement, a position, an incremental movement, a tilt angle, a translation, and/or a rotation of the input device or a portion of the input device; a voice command received by the input device; a volume level associated with the input device; a tone received by the input device; and/or a frequency of oral commands received by a microphone of the input device.

6. The computing system of claim 1, wherein the first level of interaction indicated by the first movement of the input device includes a direction of interaction with the input device, wherein the medial images are displayed at the determined rate in a direction that is determined based on the direction of interaction with the input device.

7. The computing system of claim 6, wherein the direction of interaction is forward in response to a first direction of interaction with the input device and backward in response to a second direction of interaction with the input device.

8. The computing system of claim 1, wherein the modules are further configured to:
   in response to a second movement of the input device indicating a second level of interaction:
      determine a second rate of display of medical images based on an association between the second level of interaction and one of the two or more rates of display of medical images in the selected behavior model.

9. A non-transitory computer readable medium having software modules stored thereon, the software modules configured for execution by a computing system having one or more hardware processors in order to:
   access a data structure storing conditions associated with respective behavior models, each of the behavior models indicating associations between two or more rates of display of medical images and a corresponding two or more levels of interaction, each of the two or more levels of interaction indicated by movements of an input device of the computing system;
   select a behavior model based on one or more characteristics of:
      the computing system, an environment surrounding the computing system, the display device, bandwidth available to the computing system, the medical images, a patient, a medical history of the patient, and/or an input device; and
   in response to a movement of the input device indicating a level of interaction:
      determine a rate of display of medical images based on an association between the level of interaction and one of the two or more rates of display of medical images in the selected behavior model.

10. The non-transitory computer readable medium of claim 9, wherein the software modules are further configured for execution in order to:
    identify one or more modifications that are matched by one or more characteristics, wherein one or more of the identified modifications indicate an adjustment to the determined rate of display of medical images, wherein the determined rate at which the medical images are displayed is modified by the adjustment.

11. The non-transitory computer readable medium of claim 10, wherein the adjustment indicates a percentage increase or decrease or an absolute time period.

12. The non-transitory computer readable medium of claim 10, wherein one or more of the identified modifications include a maximum rate at which the medical images are displayed.

13. The non-transitory computer readable medium of claim 9, wherein the level of interaction is determined based on one or more of an angle of a knob of the input device with reference to a neutral position; a pressure applied, a speed of movement, a position, an incremental movement, a tilt angle, a translation, and/or a rotation of the input device or a portion of the input device; a voice command received by the input device; a volume level associated with the input device; a tone received by the input device; and/or a frequency of oral commands received by a microphone of the input device.

14. The non-transitory computer readable medium of claim 9, wherein the level of interaction indicated by the first movement of the input device includes a direction of interaction with the input device, wherein the medial images are displayed at the determined rate in a direction that is determined based on the direction of interaction with the input device.

15. The non-transitory computer readable medium of claim 14, wherein the direction of interaction is forward in response to a first direction of interaction with the input device and backward in response to a second direction of interaction with the input device.

16. A method comprising:
   accessing, by a computing system having one or more hardware processors, a data structure storing conditions associated with respective behavior models, each of the behavior models indicating associations between two or more rates of display of medical images and a corresponding two or more levels of interaction, each of the two or more levels of interaction indicated by movements of an input device of the computing system;
   selecting, by the computing system, a behavior model based on one or more characteristics of:
      the computing system, an environment surrounding the computing system, the display device, bandwidth available to the computing system, the medical images, a patient, a medical history of the patient, and/or an input device; and
   in response to a movement of the input device indicating a level of interaction:
      determining, by the computing system, a rate of display of medical images based on an association between the level of interaction and one of the two or more rates of display of medical images.

17. The method of claim 16, further comprising:
   identifying one or more modifications that are matched by one or more characteristics, wherein one or more of the identified modifications indicate an adjustment to the determined rate of display of medical images, wherein the determined rate at which the medical images are displayed is modified by the adjustment.

18. The method of claim 17, wherein one or more of the identified modifications include a maximum rate at which the medical images are displayed.

19. The method of claim 16, wherein the level of interaction is determined based on one or more of an angle of a knob of the input device with reference to a neutral position; a pressure applied, a speed of movement, a position, an incremental movement, a tilt angle, a translation, and/or a rotation of the input device or a portion of the input device; a voice command received by the input device; a volume level associated with the input device; a tone received by the input device; and/or a frequency of oral commands received by a microphone of the input device.

20. The method of claim 16, wherein the level of interaction indicated by the movement of the input device includes a direction of interaction with the input device, wherein the medial images are displayed at the determined rate in a direction that is determined based on the direction of interaction with the input device.

21. The method of claim 20, wherein the direction of interaction is forward in response to a first direction of interaction with the input device and backward in response to a second direction of interaction with the input device.

* * * * *